(12) United States Patent
Hectors et al.

(10) Patent No.: US 11,969,316 B2
(45) Date of Patent: Apr. 30, 2024

(54) COMPRESSION STOCKING

(71) Applicant: TELAS B.V., Sevenum (NL)

(72) Inventors: Stefan Hectors, Sevenum (NL); Piet Smeets, Sevenum (NL); Jaap Renkema, Sittard (NL)

(73) Assignee: TELAS B.V., Sevenum (NL)

( * ) Notice: Subject to any disclaimer, the term of this patent is extended or adjusted under 35 U.S.C. 154(b) by 134 days.

(21) Appl. No.: 16/772,432

(22) PCT Filed: Dec. 11, 2018

(86) PCT No.: PCT/EP2018/084339
§ 371 (c)(1),
(2) Date: Jun. 12, 2020

(87) PCT Pub. No.: WO2019/115516
PCT Pub. Date: Jun. 20, 2019

(65) Prior Publication Data
US 2021/0069023 A1    Mar. 11, 2021

(30) Foreign Application Priority Data
Dec. 12, 2017  (EP) .................................. 17206706

(51) Int. Cl.
*A61F 13/00* (2006.01)
*A41B 11/00* (2006.01)
(Continued)

(52) U.S. Cl.
CPC ........ *A61F 13/00085* (2013.01); *A41B 11/00* (2013.01); *A41B 11/14* (2013.01);
(Continued)

(58) Field of Classification Search
CPC ......... A41B 11/00; A41B 11/08; A41B 11/06; A61F 13/08; A61F 2013/002
(Continued)

(56) References Cited

U.S. PATENT DOCUMENTS 10,007,347 B1 * 6/2018 Khoshkava ........... H01L 41/087
10,761,605 B1 * 9/2020 Sunshine ........... A41D 19/0024
(Continued)

FOREIGN PATENT DOCUMENTS

DE    202013002992 U1 * 6/2013 ............. A61F 13/08
GB          2470185 A * 11/2010 ............. A61F 13/06
(Continued)

*Primary Examiner* — Aiying Zhao
(74) *Attorney, Agent, or Firm* — Hudak, Shunk &Farine Co. LPA

(57) ABSTRACT

A compression stocking having shape memory, heat-shrinkable thermoplastic material, wherein said stocking is configured to establish, in use, a compression contact with at least one of a leg and a foot of a user upon the application of an amount of heat to the shape memory, heat-shrinkable thermoplastic material, wherein the thermoplastic material is a polymer that has a glass transition temperature below −10° C., has crystallinity with a melting temperature (Tm) between 30-50° C. and a heat of fusion of at least 10 J/g, as determined using differential scanning calorimetry (DSC) (−40° C./10.0 (K/min)/100° C.) as set out by the ASTM D3418:2003.

5 Claims, 5 Drawing Sheets

(51) Int. Cl.
- *A41B 11/14* (2006.01)
- *A61F 13/06* (2006.01)
- *A61F 13/08* (2006.01)
- *D04B 1/26* (2006.01)

(52) U.S. Cl.
CPC ........ *A61F 13/00017* (2013.01); *A61F 13/06* (2013.01); *D04B 1/26* (2013.01); *D04B 1/265* (2013.01); *A61F 2013/00195* (2013.01); *A61F 2013/002* (2013.01); *A61F 13/08* (2013.01); *Y10S 8/926* (2013.01)

(58) Field of Classification Search
USPC .......................................................... 2/239
See application file for complete search history.

(56) References Cited

U.S. PATENT DOCUMENTS

| | | | |
|---|---|---|---|
| 2012/0000251 A1* | 1/2012 | Hu | C08G 18/6674 139/384 R |
| 2013/0303957 A1* | 11/2013 | Bauerfeind | A61F 5/0111 602/76 |
| 2016/0317898 A1* | 11/2016 | Wyner | B32B 5/24 |
| 2018/0177677 A1* | 6/2018 | Pamplin | A61H 7/001 |
| 2018/0258561 A1* | 9/2018 | Khoshkava | H01L 41/193 |

FOREIGN PATENT DOCUMENTS

| | | | | |
|---|---|---|---|---|
| WO | 2017129201 A1 | 8/2017 | | |
| WO | WO-2017129201 A1 * | 8/2017 | ............... | A43B 1/00 |

\* cited by examiner

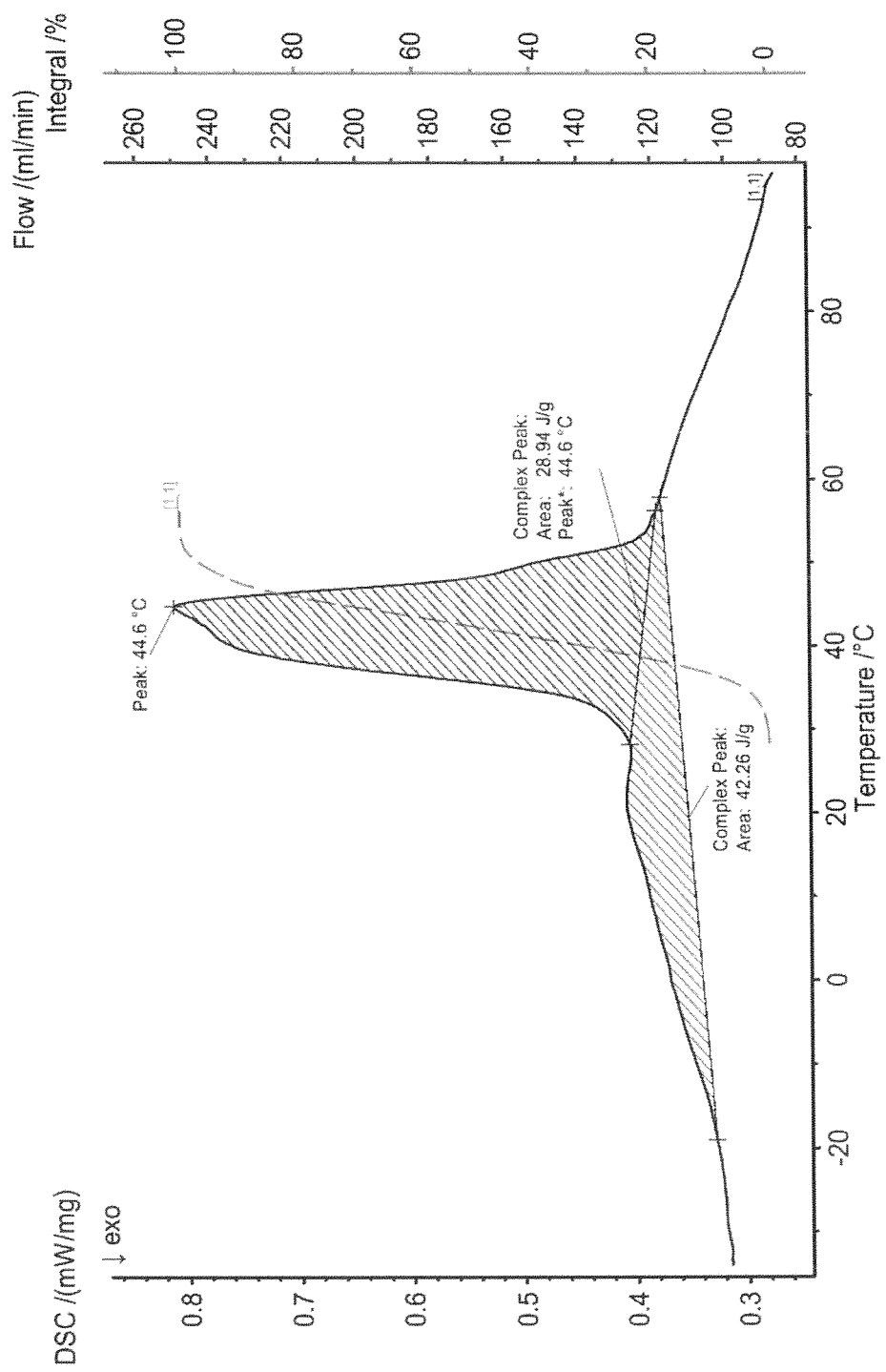

COMPRESSION STOCKING

FIELD OF THE INVENTION

The present invention relates to an improved compression stocking in terms of easier application of the compression stocking, i.e. easier putting on and off, and reduced costs.

BACKGROUND OF THE INVENTION

Advancements in the medical technologies have improved average human age, which is not only considered as an achievement of medical science but also poses new challenges. Stressful working lifestyle and long sitting hours are influencing the human blood circulation system. The consequences of this appear with increasing age. Nowadays, a large number of mostly elderly persons is suffering from venous disorders such as edema, thrombosis and varicose veins. A known and effective solution for these disorders is provided by using compression stockings. However, conventional compression stockings are associated with several disadvantages such as difficult application, i.e. arduous putting on and off of the compression stockings, and high cost. On the one hand the high costs are related to manufacture of the conventional compression stockings which includes filament spinning, filament processing to covered yarn, knitting and socks processing. On the other hand, putting on and off of conventional compression stockings without using application tools is known to be very challenging especially for elderly patients due to the highly compressive nature of the conventional compression stockings. Therefore, experienced assistants are required for helping the elderly patients in everyday life, which off course causes an additional financial burden on both patients and health insurance organizations. Consequently, there is a need for improved compression stockings that reduce the abovementioned disadvantages associated with conventional compression stockings.

SUMMARY OF THE INVENTION

It is an object of the present invention to provide a compression stocking that pre-empts or at least reduces at least one of the abovementioned and/or other disadvantages associated with compression stockings known in the art.

Aspects of the present invention are set out in the accompanying independent and dependent claims. Features from the dependent claims may be combined with features from the independent claim as appropriate and not merely as explicitly set out in the claims.

At least one of the aforementioned objects is achieved by a compression stocking consisting of a single layer film and consisting of a shape memory, heat shrinkable thermoplastic material optionally having perforations, optionally at least one attachment element, and optionally a temperature control device.

At least one of the aforementioned objects is achieved by a compression stocking consisting of a nonwoven, shape memory, heat shrinkable thermoplastic material, optionally at least one attachment element, and optionally a temperature control device.

At least one of the abovementioned objects is achieved by a compression stocking comprising shape memory, heat-shrinkable thermoplastic material, wherein said stocking is configured to establish, in use, a compression contact with at least one of a leg and a foot of a user upon the application of an amount of heat to the shape memory, heat-shrinkable thermoplastic material. The heat can be generated by at least one temperature controlling device or by the heat present in the at least one of a leg and a foot. The elastic nature and shrinkage behavior upon heating of the shape memory thermoplastic material is used to provide a tailor-made compression stocking.

Upon application the compression stocking has a larger circumference than at least one of a leg and a foot of a user. This allows the compression stocking to be arranged easy and therefore fast around at least one of the legs and the feet of a user. Upon putting on the compression stocking, it comes into contact with at least one of the legs and the feet of the user. The compression stocking is configured to shrink as a consequence of the application of an amount of heat by for example at least one temperature controlling device. As a result of the shape memory of the heat-shrinkable thermoplastic material, the compression stocking assumes its original shape and establishes a compression contact with at least one of the legs and the feet of the user.

The most important parameter for achieving an adjustable, temperature-dependent stress control of the shape memory, heat-shrinkable thermoplastic material is the melting temperature (Tm) of the polymer.

The thermoplastic material is a polymer characterized in that it has a glass transition temperature below $-10°$ C., preferably below $-20°$ C., most preferably below $-30°$ C., has crystallinity with a melting temperature (Tm) between 30-50° C. and a heat of fusion of at least 10 J/g, preferably at least 15 J/g, most preferably at least 20 J/g and preferably no crystallinity between 60-80° C.

The glass transition temperature (Tg), melting temperature and heat of fusion of the thermoplastic polymer is determined using differential scanning calorimetry (DSC) ($-40°$ C./10.0 (K/min)/100° C.) as set out by the ASTM D3418:2003. The heat of fusion (J/g) is determined by calculating the surface area under the $1^{st}$ cooling curve (DSC) between the two points at which the $1^{st}$ cooling curve deviates from the relatively straight baseline, for example between $-20$-80° C., preferably between 30-50° C.

In a preferred embodiment of the compression stocking according to the present invention, the shape memory, heat-shrinkable thermoplastic material comprises thermoplastic polyurethane-polyester (TPU-Polyester).

For application in the compression stocking the TPU-Polyester is stretched (drawn) from its first state to a second state in which it has a size that can be for example 10 to 200% larger in circumference than that of at least one of a leg and a foot of a user.

The shape memory heat-shrinkable thermoplastic material is characterized in that it can have at least one shape memory state (first state) and a second state, which is the thermoplastic polymer after stretching.

The thermoplastic polymer is subject to two interaction mechanisms. The first interaction mechanism is active between 30-50° C. and characterized by crystallinity. The second interaction mechanism is at least active at temperatures above the melting temperature, for example between 50-100° C., preferably between 51-80° C. The second interaction mechanism is characterized by at least one of the following mechanisms: crosslinks (covalent bonds), hydrogen bonds and crystallinity at high temperature, for example above 80° C., preferably above 100° C.

Upon heating of the first state thermoplastic polymer to the melting temperature, for example to 50-60° C., the first interaction mechanism is deactivated. The heated first state thermoplastic polymer can then be stretched to the second state, while the second interaction mechanism preserves the memory of the first state. Then the thermoplastic polymer is cooled, while holding in the second state (stretched), which cooling re-activates the first interaction mechanism (crystallization between 30-50 celc) and maintains the strained thermoplastic polymer in the second state.

Therefore, the TPU-Polyester should significantly shrink upon exposure to heat at or above the melting temperature of the thermoplastic material and provide the required compression contact to at least one of the legs and the feet of the user.

Furthermore, regarding the design of the compression stocking it is advantageous to apply TPU-Polyester material having highly elastic properties close to bending body parts such as the knees and ankles of the user to maintain the required compression effect.

In an embodiment of the compression stocking according to the present invention, the temperature controlling device comprises at least one of a heating arrangement that is integrated in the compression stocking and an external heating arrangement. Both types of heating arrangements can comprise resistive heating elements for providing an amount of heat that is sufficient to surpass the melting temperature of the shape memory, heat-shrinkable thermoplastic material used.

In an embodiment of the compression stocking according to the present invention, at least one of the heating arrangements that is integrated in the compression stocking and the external heating arrangement is configured to generate heat using at least one of electrical energy and chemical energy. The electrical energy can be provided by at least one battery that is at least one of embroidered in the compression stocking and arranged externally of the compression stocking. The at least one battery is associated with the aforementioned resistive heating elements. It is also conceivable that a chemical exothermic reaction is used to provide an amount of heat that is sufficient to surpass the melting temperature of the shape memory, heat-shrinkable thermoplastic material to establish the required compression effect.

In an embodiment of the compression stocking according to the present invention, the compression stocking has one of a tubular shape and an anatomical shape in accordance with at least one of the legs and the feet of the user.

In an embodiment of the compression stocking according to the present invention, when the compression stocking is in use, the shape memory, heat-shrinkable thermoplastic material is at least partially arranged around at least one of the legs and the feet of the user. In this way, the compression stocking can comprise different zones, i.e. zones comprising shape memory, heat-shrinkable thermoplastic material and zones of material that does not shrink under the influence of at least one of bodily heat and heat generated by a temperature controlling device.

In a preferred embodiment of the compression stocking according to the present invention, the shape memory, heat-shrinkable thermoplastic material has crystallinity with a melting temperature (Tm) between 30-50° C. and a heat of fusion of at least 10 J/g, preferably at least 15 J/g, most preferably at least 20 J/g.

In an embodiment of the compression stocking according to the present invention, the shape memory, heat-shrinkable thermoplastic material is arranged as at least one of a mesh, a yarn and a film.

In a preferred embodiment the compression part of the stocking is a nonwoven material, it is preferably obtained by extrusion of the thermoplastic material into a film or hose that is formed into a stocking.

In a preferred embodiment of the compression stocking according to the present invention, the shape memory, heat-shrinkable thermoplastic material comprises a TPU-polyester sold under the tradename Desmopan 2795A. In the case that the compression stocking comprises TPU-Polyester mesh, the elastic nature and shrinkage behavior on heating of the TPU-Polyester mesh will be used. The TPU-Polyester polymer can be extruded with a rotating spinneret, which allows the entanglement of TPU-Polyester filaments in mesh form. The extruded TPU-Polyester mesh is used to make a tailor-made compression stocking having a size that is larger than the size of at least one of a leg and a foot of a user. This allows easy and therefore fast putting on of the compression stocking. Upon putting on the compression stocking, the TPU-Polyester polymer absorbs heat from at least one of the legs of the user, the feet of the user and a temperature controlling device and shrinks. The shrinkage in the TPU-Polyester mesh leads to the required compression effect. Thus, TPU-Polyester mesh can be directly used as compression textile.

In the case that the compression stocking comprises yarn the properties of the yarn used that are important for ensuring a good performance of the compression stocking include weight per unit area, thickness of the knitted fabric, tensile strength, bending properties, air permeability, hydrophilic nature and moisture management properties, and compression properties.

In the case that the compression stocking comprises TPU-Polyester film the properties of the TPU-Polyester film used that are important for ensuring a good performance of the compression stocking include film thickness, melting temperature of the TPU-Polyester material, temperature dependent shrinkage properties, temperature at which shrinkage begins, correlation between the amount of shrinkage depending on operating temperature, overall shrinkage at various temperatures, elastic properties, elastic recovery, change in elasticity with temperature treatment, air permeability, and moisture management properties, e.g. moisture content and wicking properties.

In an embodiment of the compression stocking according to the present invention, the film of shape memory, heat-shrinkable thermoplastic material has a thickness of 0.005 mm-0.5 mm, preferably 0.01 mm-0.2 mm. The shrinkage and the resulting compression effect of the TPU-Polyester film depends on the internal shear stresses in the polymer. Thinner TPU-Polyester films have higher levels of internal stresses due to a comparative higher level of drawing and thus have a higher level of compression. Furthermore, thicker TPU-Polyester films have an increased hardness and lack of flexibility, which reduces the bending properties of the TPU-Polyester film. The lack of bending properties affects the comfort properties of TPU-Polyester film based compression stockings. Therefore, thinner TPU-Polyester films in the range of 0.01 mm-0.2 mm are favorable for application in TPU-Polyester film based compression stocking.

In an embodiment of the compression stocking according to the present invention, the film of shape memory, heat-shrinkable thermoplastic material is provided with perforations. In this way, the comfort properties of the compression stocking can be improved as films without perforations are known to differ significantly from woven/nonwoven textile structures because of significant differences in the air permeability and moisture transport properties. The comfort level of a compression textile product is a major influencing factor for its acceptance by the user and therefor for its use. The gas permeability of films of shape memory, heat-shrinkable thermoplastic material is typically in a range between 0.0094-352 m/s Hg, which is considerably lower than the gas permeability of knitted fabrics. The gas permeability of knitted fabrics conventionally used for socks is typically in a range between 152-1812 mm/s Hg. The porous structure of knitted fabrics allows good moisture transport and sweat absorption. This cannot be expected in the case of films. Therefore, the film of shape memory, heat-shrinkable thermoplastic material is provided with perforations in order to improve the moisture handling capability and the breathability and consequently the comfort level of the compression stocking.

In an embodiment of the compression stocking according to the present invention, the compression stocking comprises a woven fabric comprising knitting thread that is provided with insertion thread comprising a core yarn of the shape memory, heat-shrinkable thermoplastic material, the insertion thread being part of at least one of the heating arrangements that is integrated in the compression stocking and the external heating arrangement. Upon absorbing heat generated by at least one of the heating arrangements, the insertion thread will shrink when the melting temperature of the core yarn of shape memory, heat-shrinkable thermoplastic material, e.g. TPU-Polyester, is surpassed. Consequently, the required compression effect of the compression stocking can be achieved.

In an embodiment of the compression stocking according to the present invention, the insertion thread further comprises electrically conductive yarn and insulation yarn, the electrically conductive yarn being arranged between the core yarn and the insulation yarn and being associated with an electrical power source of at least one of the heating arrangements that is integrated in the compression stocking and the external heating arrangement. When the heat generated by at least one of the legs and the feet of the user is not sufficient to surpass the melting temperature of the core yarn of shape memory, heat-shrinkable thermoplastic material, e.g. TPU-Polyester, the required temperature-dependent compression effect of the compression stocking can be achieved by activating the electrically conductive yarn in order to generate additional heat by way of Ohmic resistance heating. By further cladding the electrically conductive yarn with an insulation yarn, the heating will only affect the core yarn while at least one of the legs and the feet of the user is unaffected. In this way, burning of at least one of the legs and the feet of the user can be avoided and the level of comfort of wearing the compression stocking can be preserved. The electrical power source that is associated with the electrically conductive yarn can be a battery that is incorporated into the compression stocking, e.g. via stitching.

The compression stocking according to this embodiment enables easy putting on and off and provides time—as well as temperature-constant compression functionality. During putting on the compression stocking, the battery is switched off and the core yarn stays below its melting temperature. In order to generate the compression effect, the battery will be switched on thus proving electrical current for Ohmic resistive heating. Upon absorption of the heat generated, the core yarn of shape memory, heat-shrinkable thermoplastic material, e.g. TPU-Polyester, will reach a temperature above its melting temperature causing the material to trigger its compressive nature. If the stocking material is to be put off, resistive heating is terminated leading to a relaxing of the core yarn of shape memory, heat-shrinkable thermoplastic material. As a consequence, the compression stocking can be put off easily and therefore fast.

In an embodiment of the compression stocking according to the present invention, the compression stocking comprises a leg part and a foot part that are one of detachably associated with each other via at least one attachment element and fixedly connected to each other. When the compression stocking comprises a leg part and a foot part that are detachably associated with each other via at least one attachment element, it is possible to apply at least one of the leg parts and the foot parts according to the needs of the user.

In an embodiment of the compression stocking according to the present invention, the temperature controlling device in at least one of the leg parts and the foot parts is configured and arranged to be controllable by an electronic controlling device. In this way, the compression effects in at least one of the leg parts and the foot parts can be adjusted independently from each other. Hence, local pressure control in the compression stocking can be improved. The temperature controlling device can be operated by the electronic controlling device via at least one of a wired and wireless connection. As a result, the performance of the compression stocking can be improved.

In an embodiment of the compression stocking according to the present invention, the compression stocking is a single-use compression stocking. Single-use compression stockings made of cheap raw materials and fabricated in accordance with cost-effective production technologies provide an alternative to compression stockings known in the art.

BRIEF DESCRIPTION OF THE DRAWINGS

Further features and advantages of the present invention will become apparent from the description of the present invention by way of exemplary and non-limiting embodiments of a compression stocking according to the present invention.

The person skilled in the art will appreciate that the described embodiments are exemplary in nature only and not to be construed as limiting the scope of protection in any way. The person skilled in the art will realize that alternatives and equivalent embodiments of the compression stocking can be conceived and reduced to practice without departing from the scope of protection of the present invention.

Reference will be made to the figures on the accompanying drawing sheets. The figures are schematic in nature and therefore not necessarily drawn to scale. Furthermore, equal reference numerals denote equal or similar parts. On the attached drawing sheets.

FIG. 7 shows the typical differential scanning calorimetry (DSC) $1^{st}$ cooling curve for the TPU-Polyester sheet of the compression stocking according to the present invention.

DETAILED DESCRIPTION OF EMBODIMENTS

Figure 1A:
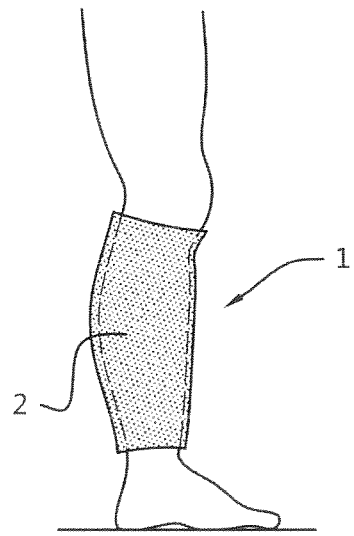
FIG. 1A shows a schematic side view of a leg of a user around which a first exemplary, non-limiting embodiment of a compression stocking according to the present invention is arranged before absorption of heat generated by at least one of the legs of the user and a temperature controlling device.

FIG. 1A shows a schematic side view of a leg of a user around which a first exemplary, non-limiting embodiment of a compression stocking 1 according to the present invention is arranged before the compression stocking 1 has absorbed heat generated by at least one of the temperature controlling devices. As can be seen in FIG. 1A, upon application the anatomically shaped compression stocking 1 has a larger circumferential size than the part of the leg of the user around which it is to be arranged. This allows the user to put on the compression stocking 1 in an easy and fast way without any help. In this way, at least the costs of putting on the compression stocking 1 can be reduced.

The compression stocking 1 comprises shape memory, heat-shrinkable thermoplastic material 2, e.g. TPU-Polyester, that is configured to shrink upon absorbing an amount of heat that is sufficient to increase the temperature of the shape memory, heat-shrinkable thermoplastic material 2 above its melting temperature as has been explained above.

Figure 1B:
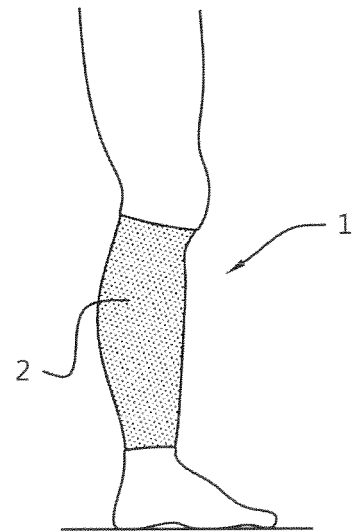
FIG. 1B shows a schematic side view of the leg of the user around which the first exemplary, non-limiting embodiment of the compression stocking is arranged in a compression contact after absorption of heat generated by at least one of the temperature controlling devices.

FIG. 1B shows a schematic side view of the leg of the user around which the first exemplary, non-limiting embodiment of the compression stocking 1 is arranged after absorption of heat generated by the leg of the user. As a result of the shape memory of the heat-shrinkable thermoplastic material 2, the compression stocking 1 has assumed its original shape and establishes a compression contact with the leg of the user.

Figure 2:
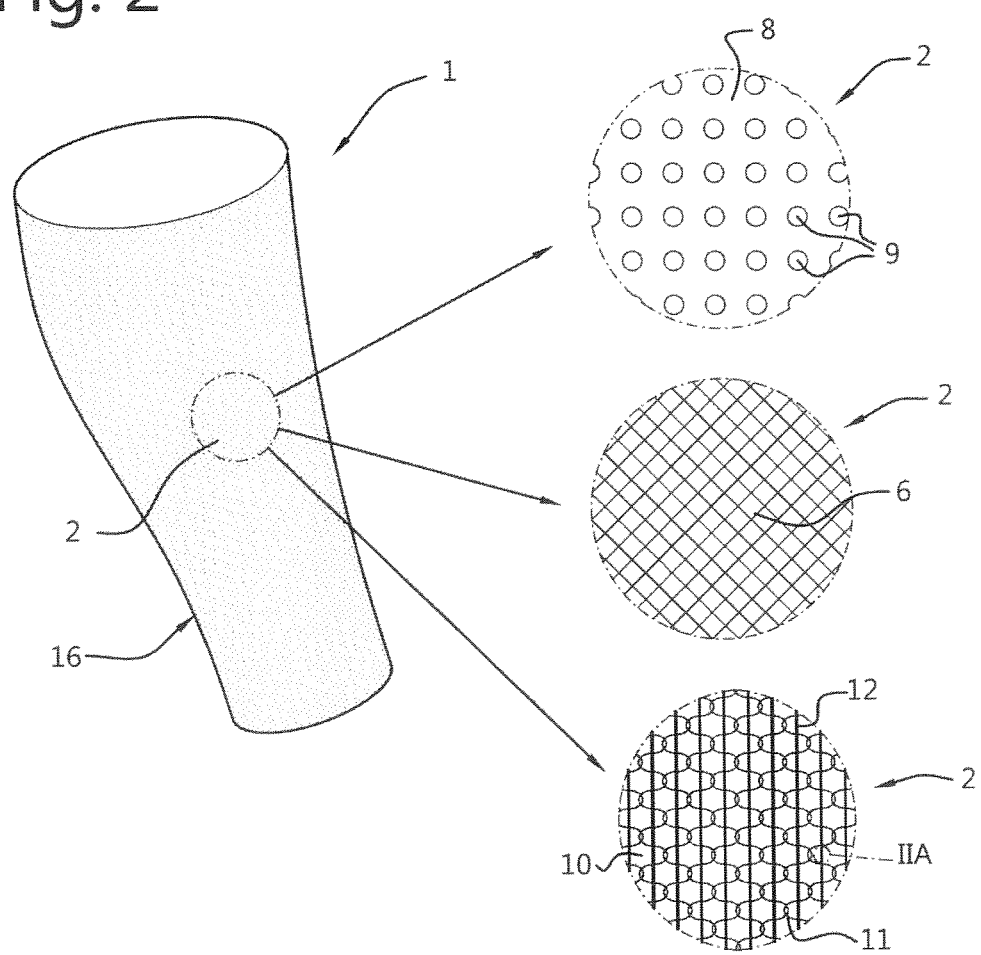
FIG. 2 shows details regarding different arrangements of the shape memory, heat-shrinkable thermoplastic material of the compression stocking according to the invention.

FIG. 2 shows details regarding different arrangements of the shape memory, heat-shrinkable thermoplastic material 2. In an exemplary, non-limiting embodiment of the compression stocking 1 according to the present invention the shape memory, heat-shrinkable thermoplastic material 2, e.g. TPU-Polyester, can be arranged as a mesh 6. As explained above, upon putting on the compression stocking 1, the TPU-Polyester polymer can absorb heat from at least one of the temperature controlling devices and shrinks. The shrinkage in the TPU-Polyester mesh 6 leads to the required compression effect. Thus, TPU-Polyester mesh 6 can be directly used as compression textile.

In another exemplary, non-limiting embodiment of the compression stocking 1 according to the invention the shape memory, heat-shrinkable thermoplastic material 2, e.g. TPU-Polyester, can be arranged as a film 8 that is provided with perforations 9. As described above, the perforations 9 are advantageous for improving the comfort properties of the compression stocking 1 and acceptance of the compression stocking 1 by users because TPU-Polyester films 8 without perforations are known to differ significantly from woven/nonwoven textile structures because of significant differences in the air permeability and moisture transport properties.

In yet another exemplary, non-limiting embodiment of the compression stocking 1 according to the invention the shape memory, heat-shrinkable thermoplastic material 2, e.g. TPU-Polyester, can be arranged as a fabric 10. The woven fabric 10 comprises knitting thread 11 that is provided with insertion thread 12 that is part of a temperature controlling device. This aspect will be elucidated in relation to FIG. 3A.

Figure 2A:
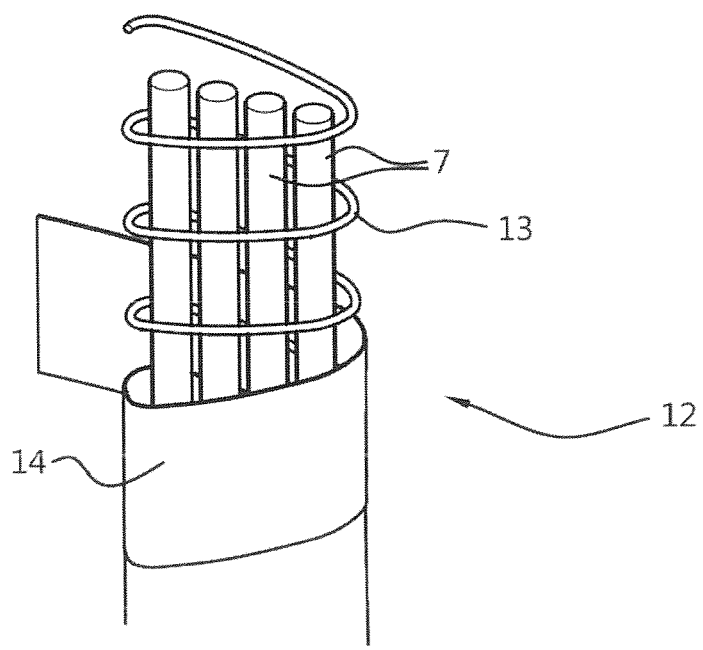
FIG. 2A shows a detail of an insertion thread comprising shape memory, heat-shrinkable thermoplastic material.

FIG. 2A shows a detail of the insertion thread 12 that comprises a TPU-Polyester core yarn 7, electrically conductive yarn 13 and insulation yarn 14. The electrically conductive yarn 13 is arranged between the TPU-Polyester core yarn 7 and the insulation yarn 14.

Figure 3:
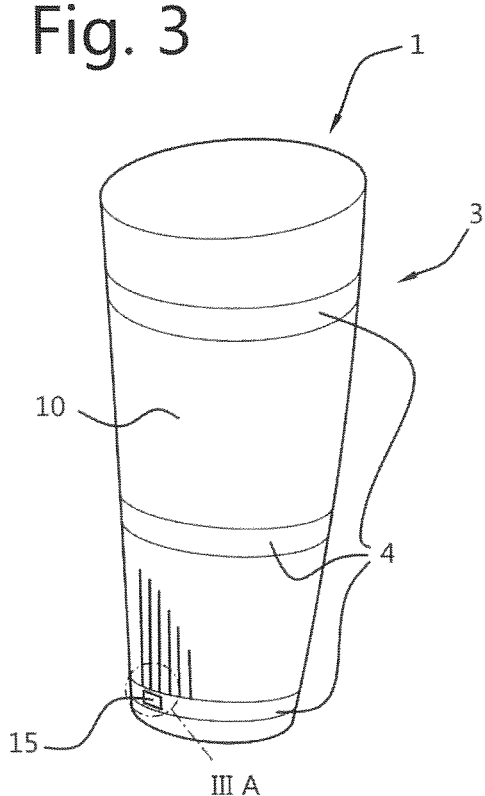
FIG. 3 shows a schematic perspective view of a second exemplary, non-limiting embodiment of the compression stocking according to the invention.

FIG. 3 shows a schematic perspective view of a second exemplary, non-limiting embodiment of the compression stocking 1 according to the invention. The compression stocking 1 has a tubular shaped leg part without a foot part. The compression stocking 1 is provided with a temperature controlling device 3 that according to a first exemplary, non-limiting embodiment comprises a heating arrangement 4 that is integrated in the compression stocking 1. The heating arrangement 4 comprises an electrical power source 15, e.g. a battery or a battery pack. If bodily generated heat is insufficient to increase the temperature of the material 2 above its melting temperature, the heating arrangement 4 of the temperature controlling device 3 can be used to provide a sufficient amount of heat to surpass the melting temperature. It would of course also be possible to provide heat generated by an external heating arrangement but according to this embodiment of the compression stocking 1 that would not be necessary.

In another exemplary, non-limiting embodiment of the compression stocking 1 according to the invention, the compression stocking 1 could be provided with a temperature controlling device 3 that comprises an integrated heating arrangement that is configured to provide heat generated by a chemical exothermic reaction.

Figure 3A:
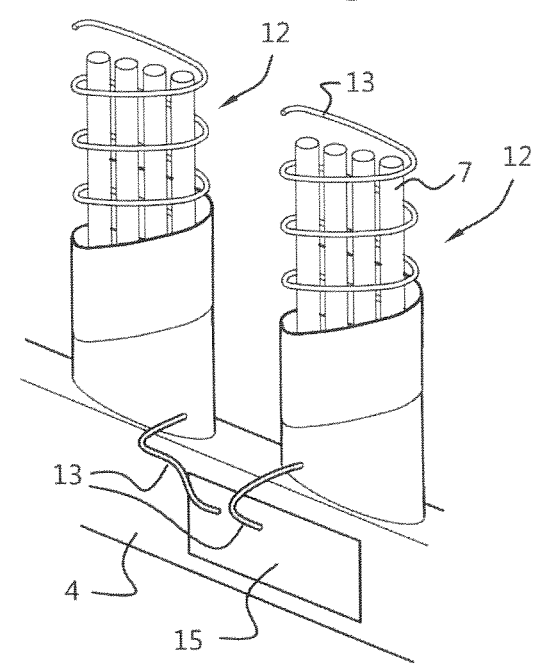
FIG. 3A shows a detailed view of an exemplary, non-limiting embodiment of a heating arrangement that is integrated in the compression stocking shown in FIG. 3.

FIG. 3A shows an exemplary, non-limiting embodiment of how the electrically conductive yarn 13 can be associated with the electrical power source 15 of the heating arrangement 4. However, the electrically conductive yarn 13 can also be associated with an electrical power source of an external heating arrangement.

Figure 4:
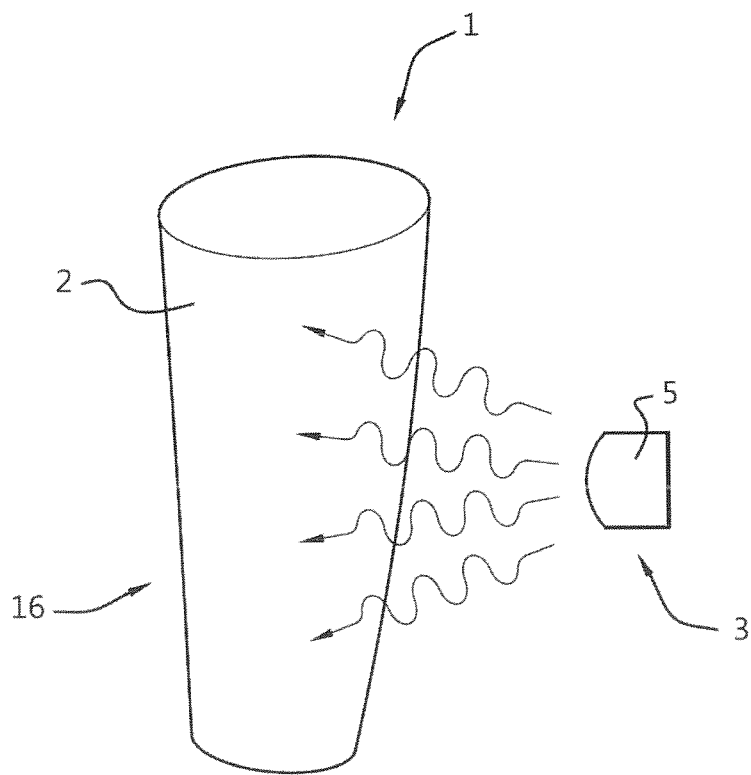
FIG. 4 shows a schematic perspective view of a third exemplary, non-limiting embodiment of the compression stocking according to the invention.

FIG. 4 shows a schematic perspective view of a third exemplary, non-limiting embodiment of the compression stocking 1 according to the invention. The compression stocking 1 has a tubular shape and is not provided with an integrated heating arrangement. A temperature controlling device 3 to increase the temperature of the shape memory, heat-shrinkable thermoplastic material 2 above its melting temperature and thereby shrink it, can be used. According to a second exemplary, non-limiting embodiment the temperature controlling device 3 comprises an external heating arrangement 5 that can for example be a hair dryer or an infrared (IR) light source.

Figure 5A:
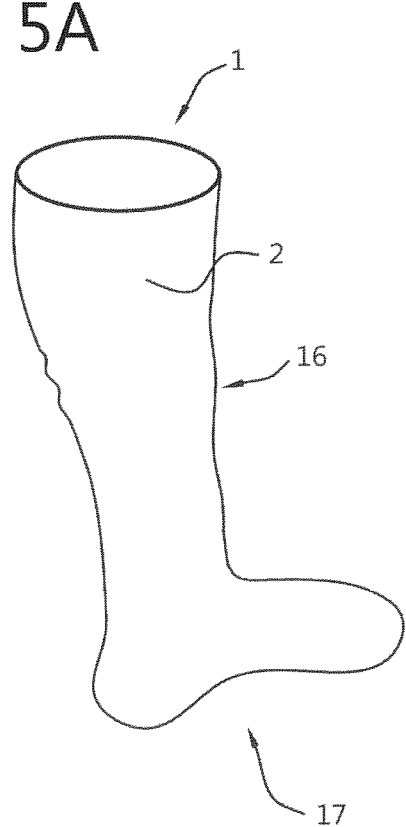
FIG. 5A shows a schematic perspective view of a fourth exemplary, non-limiting embodiment of the compression stocking according to the invention.

FIG. 5A shows a schematic perspective view of a fourth exemplary, non-limiting embodiment of the compression stocking 1 according to the invention. The compression stocking 1 comprises a leg part 16 that is anatomically shaped and a foot part 17 that can have one of an anatomic shape and a tubular shape. The leg part 16 and the foot part 17 are fixedly connected to each other.

Figure 5B:
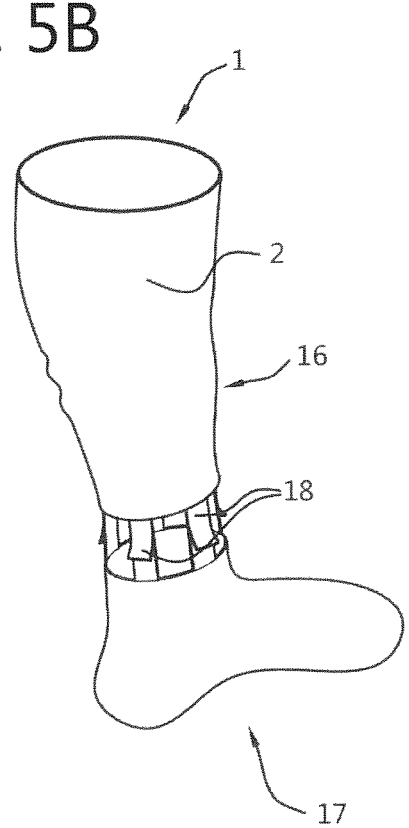
FIG. 5B shows a schematic perspective view of a fifth exemplary, non-limiting embodiment of the compression stocking according to the invention.

FIG. 5B shows a schematic perspective view of a fifth exemplary, non-limiting embodiment of the compression stocking 1 according to the invention. The compression stocking 1 comprises a leg part 16 that is anatomically shaped and a foot part 17 that can have one of an anatomic shape and a tubular shape. The leg part 16 and the foot part 17 are detachably associated with each other via attachment elements 18, with strip fasteners being illustrated. The configuration of the compression stocking 1 according to this embodiment enables to apply at least one of the leg parts 16 and the foot parts 17 according to the needs of the user.

Figure 5C:
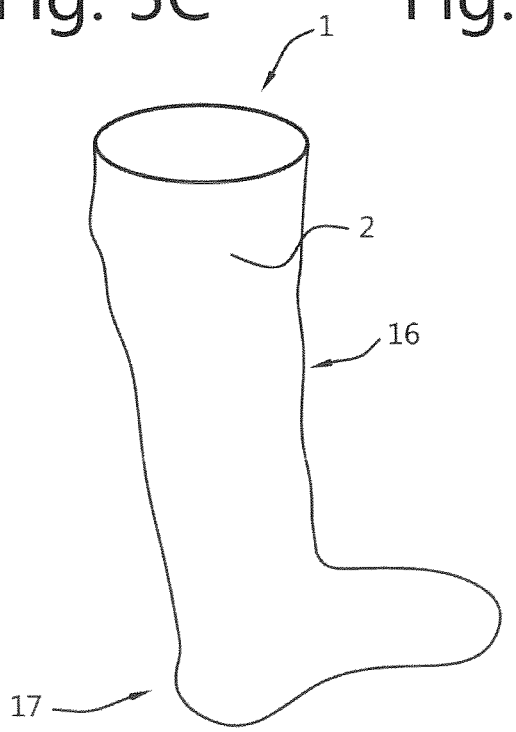
FIG. 5C shows a schematic perspective view of a sixth exemplary, non-limiting embodiment of the compression stocking according to the invention.

FIG. 5C shows a schematic perspective view of a sixth exemplary, non-limiting embodiment of the compression stocking 1 according to the invention. The compression stocking 1 comprises a leg part 16 that has a tubular shape and a foot part 17 that can have one of an anatomic shape and a tubular shape. The leg part 16 and the foot part 17 are fixedly connected to each other.

Figure 5D:
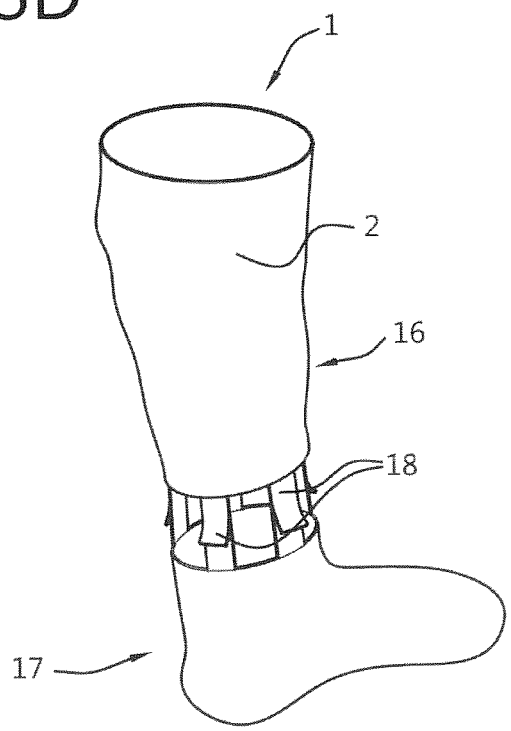
FIG. 5D shows a schematic perspective view of a seventh exemplary, non-limiting embodiment of the compression stocking according to the invention.

FIG. 5D shows a schematic perspective view of a seventh exemplary, non-limiting embodiment of the compression stocking 1 according to the invention. The compression stocking 1 comprises a leg part 16 that has a tubular shape and a foot part 17 that can have one of an anatomic shape and a tubular shape. The leg part 16 and the foot part 17 are detachably associated with each other via attachment elements 18, with strip fasteners being illustrated. The configuration of the compression stocking 1 according to this embodiment enables to apply at least one of the leg parts 16 and the foot parts 17 according to the needs of the user.

Figure 6:
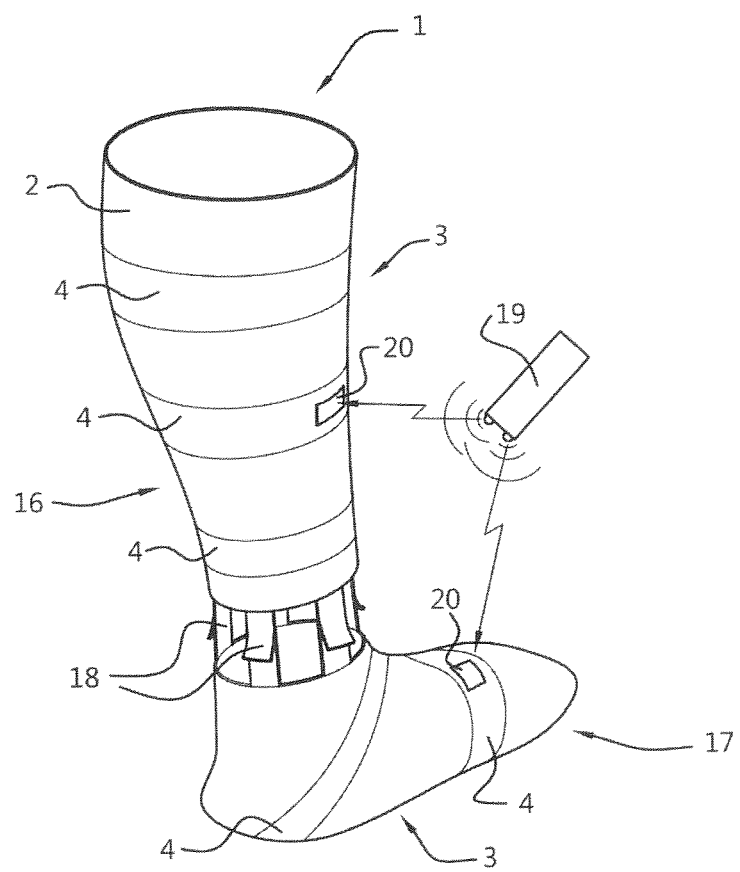
FIG. 6 shows a schematic perspective view of an eighth exemplary, non-limiting embodiment of the compression stocking according to the present invention.

FIG. 6 shows a schematic perspective view of an eighth exemplary, non-limiting embodiment of the compression stocking 1 according to the invention. The compression stocking 1 comprises a leg part 16 and a foot part 17 that are detachably associated with each other via attachment elements 18, with strip fasteners being illustrated. The leg part 16 and the foot part 17 are each provided with a temperature controlling device 3 that each comprise a respective integrated heating arrangement 4. At least one of the temperature controlling device 3 in the leg part 16 and the temperature controlling device 3 in the foot part 17 can be configured and arranged to be controllable by an electronic controlling device 19 via one of a wired and a wireless connection. In the embodiment of the compression stocking 1 shown in FIG. 6, both the temperature controlling device 3 in the leg part 16 and the temperature controlling device 3 in the foot part 17 are provided with a respective electronic activation device 20 that is configured to receive a control signal from the electronic control device 19. Upon receipt of a control signal from the electronic control device 19 at least one of the electronic activation device 20 of the temperature controlling device 3 of the leg part 16 and the electronic activation device 20 of the temperature controlling device 3 of the foot part 17 activates at least one of the corresponding heating arrangements 4 integrated in the leg part 16 and the corresponding heating arrangement 4 integrated in the foot part 17 to generate heat or deactivates at least one of the corresponding heating arrangements 4 integrated in the leg part 16 and the corresponding heating arrangement 4 integrated in the foot part 17 to stop generating heat. In this way, the compression effects in at least one of the leg parts 16 and the foot parts 17 can be adjusted independently from each other. Hence, local pressure control in the compression stocking 1 can be improved.

FIG. 7 shows the $1^{st}$ cooling DSC curve of a TPU-Polyester preferably used in the present invention. An example of such TPU-Polyester is Desmopan 2795A. The TPU-Polyester is characterized in that it has a glass transition temperature below −10° C., preferably below −20° C., most preferably below −30° C., has crystallinity with a melting temperature (Tm) between 30-50° C. and a heat of fusion of at least 10 J/g, preferably at least 15 J/g, most preferably at least 20 J/g and no crystallinity between 60-80° C.

The present invention can be summarized as relating to a compression stocking 1 comprising shape memory, heat-shrinkable thermoplastic material 2, wherein said stocking is configured to establish, in use, a compression contact with at least one of a leg and a foot of a user upon the application of an amount of heat to the shape memory, heat-shrinkable thermoplastic material generated by at least one of the leg of the user, the foot of the user and a temperature controlling device 3.

It will be clear to a person skilled in the art that the scope of the present invention is not limited to the examples discussed in the foregoing but that several amendments and modifications thereof are possible without deviating from the scope of the present invention as defined by the attached claims. In particular, combinations of specific features of various aspects of the invention may be made. An aspect of the invention may be further advantageously enhanced by adding a feature that was described in relation to another aspect of the invention. While the present invention has been illustrated and described in detail in the figures and the description, such illustration and description are to be considered illustrative or exemplary only, and not restrictive.

The present invention is not limited to the disclosed embodiments. Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. The mere fact that certain measures are recited in mutually different dependent claims does not indicate that a combination of these measures cannot be used to advantage. Any reference numerals in the claims should not be construed as limiting the scope of the present invention.

REFERENCE NUMERALS 1 compression stocking
2 shape memory, heat-shrinkable thermoplastic material
3 temperature controlling device
4 heating arrangement that is integrated in the compression stocking
5 external heating arrangement
6 mesh of shape memory, heat-shrinkable thermoplastic material
7 core yarn of shape memory, heat-shrinkable thermoplastic material
8 film of shape memory, heat-shrinkable thermoplastic material
9 perforations
10 woven fabric
11 knitting thread
12 insertion thread
13 electrically conductive yarn 14 insulation yarn
15 electrical power source
16 leg part of compression stocking
17 foot part of compression stocking
18 attachment element
19 electronic controlling device
20 electronic activation device

What is claimed is:

1. A compression stocking, consisting of:
1) a nonwoven, shape memory, heat-shrinkable thermoplastic material,
2) optionally at least one attachment element, and
3) optionally a temperature controlling device,
wherein said stocking is configured to establish, in use, a compression contact with at least ne of a leg and a foot of a user upon an application of an amount of heat to the shape memory, heat-shrinkable thermoplastic material, wherein the thermoplastic material is a polymer that has a glass transition temperature below −10° C., has crystallinity with a melting temperature (Tm) between 30-50° C. and a heat of fusion of at least 10 J/g, as determined using differential scanning calorimetry (DSC) (−40° C./10.0 (K/min)/100° C.) as set out by the ASTM D3418:2003.

2. The compression stocking according to claim 1, wherein the thermoplastic polymer has at least one of the shape memory mechanisms: crosslinks (covalent bonds), hydrogen bonds and crystallinity at a temperature above 80° C.

3. The compression stocking according to claim 2, wherein the polymer does not have crystallinity between 60-80° C.

4. The compression stocking according to claim 3, wherein the thermoplastic polymer is a polyurethane-polyester (TPU-Polyester).

5. The compression stocking according to claim 4, wherein the temperature controlling device is present in the compression stocking and comprises at least one of i) a heating arrangement that is integrated in the compression stocking and ii) an external heating arrangement; wherein the at least one of i) the heating arrangement that is integrated in the compression stocking and ii) the external heating arrangement is configured to generate heat using at least one of electrical energy and chemical energy; and wherein a leg part and a foot part of the compression stocking are one of i) detachably associated with each other via the at least one attachment element that is a strip fastener and ii) fixedly connected to each other.

* * * * *

UNITED STATES PATENT AND TRADEMARK OFFICE
CERTIFICATE OF CORRECTION

| | | |
|---|---|---|
| PATENT NO. | : 11,969,316 B2 | Page 1 of 1 |
| APPLICATION NO. | : 16/772432 | |
| DATED | : April 30, 2024 | |
| INVENTOR(S) | : Stefan Hectors et al. | |

It is certified that error appears in the above-identified patent and that said Letters Patent is hereby corrected as shown below:

In the Claims

In Claim 1, Column 11, Line 16, delete "ne" and insert -- one --.

In Claim 1, Column 11, Line 23, delete "Jig" and insert -- J/g --.

Signed and Sealed this
Second Day of July, 2024

Katherine Kelly Vidal
*Director of the United States Patent and Trademark Office*